United States Patent [19]

Mohammed et al.

[11] 4,249,943
[45] Feb. 10, 1981

[54] NON-PRECIOUS CERAMIC ALLOY

[75] Inventors: M. Hamdi A. Mohammed, Gainesville, Fla.; Dwarika P. Agarwal, Williamsville; Clyde E. Ingersoll, Tonawanda, both of N.Y.

[73] Assignee: Williams Gold Refining Company Incorporated, Buffalo, N.Y.

[21] Appl. No.: 950,430

[22] Filed: Oct. 11, 1978

[51] Int. Cl.³ .............................................. C22C 19/05
[52] U.S. Cl. ..................................... 75/171; 433/200; 433/207
[58] Field of Search .................. 75/171, 170; 32/2, 8; 433/200, 207

[56] References Cited

U.S. PATENT DOCUMENTS

| | | | |
|---|---|---|---|
| 3,510,294 | 5/1970 | Bieber et al. | 75/171 |
| 3,859,060 | 1/1975 | Eiselstein et al. | 75/171 |
| 3,969,111 | 7/1976 | Acuncius et al. | 75/171 |
| 4,080,201 | 3/1978 | Hodge et al. | 75/171 |

Primary Examiner—R. Dean
Attorney, Agent, or Firm—Christel, Bean & Linihan

[57] ABSTRACT

An alloy composition for dental use containing, by weight, aluminum 0–3.0%, cobalt 0–20.0%, chromium 10.0–20.0%, manganese 0–1.5%, molybdenum 6.0–18.0%, nickel 58.5–77.0% and silicon 0–2.0%. The alloy retains the corrosion resistance properties found in nickel-chromium base alloys while having reduced yield strength typical of gold alloys thereby resulting in greater ease of grinding, polishing and manipulation. The alloy finds use as a porcelain substrate alloy and also as a crown and bridge or partial denture alloy.

6 Claims, No Drawings

NON-PRECIOUS CERAMIC ALLOY

BACKGROUND OF THE INVENTION

This invention relates to the art of metal alloys, and more particularly to a new and improved alloy for dental casting.

Metals and metal alloys are used extensively in restorative and corrective dentistry. For example, it has been long known to replace a tooth or a portion of a tooth with a metal appliance to restore the function of the tooth by restoring its contour and/or the incisal, occlusal or chewing surface.

In previous inventions, it was taught that an alloy for crown and bridge applications should possess low yield strength and high ductility, both properties being essential for burnishing the alloy within the mouth using dental hand instruments. Accordingly, alloys containing major quantities of cobalt and necessarily free from molybdenum and carbon were developed.

A special area of dental crown and bridge applications is one where the tooth to be restored is in the visible region of the mouth and where aesthetics are equally important to function. In this event the dentist does not only prepare a metallic casting but instead prepares a coping in the form of a thin "shell-like" crown on which surface a dental ceramic is baked to produce the so called ceramo-metal crown. For such a specialized area of dental crown and bridge practice the burnishability of the alloy, while still significant, is a less important metal quality. The two metal qualities of great significance to ceramo-metal restorations are ability of the metal to chemically bond and maintain its adherence to the ceramic coating, and the ability of the metal to attain such a bond to the ceramic coating at high temperatures without the migration of the constituents of the alloy into the ceramic coating causing its discoloration.

The bonding of the metal to the ceramic coating is due to the chemical interaction between the ceramic oxides and surface oxides on the metal coping. Such bonding takes place at high temperatures. As the composite restoration is cooled down to room temperature, the ceramic coating and the metal coping must contract at compatible rates. In other words, both the metal and the ceramic should possess compatible coefficients of thermal expansion. Should there be a differential between the two rates of contraction of the metal and the ceramic, the bond between them breaks and the restoration fails.

Accordingly, a most important feature in the design of a metal alloy for dental ceramo-metal applications is to compound it such that the compositional chemistry of the alloy can repeatedly produce a precisely-determined coefficient of thermal contraction. Further, minor variations in the percentage of the element most responsible for controlling the coefficient of thermal expansion in the alloy should not cause perceptible variation in such coefficient. This invention discloses the discovery of such an alloy design where the coefficient of thermal expansion and contraction of the metal can be precisely controlled and where minor alloying variations from a melt to a melt, in preparation for commercial use, will have no perceptible effect on such coefficient.

The ability of the alloy to bond to ceramics at high temperature without the metal discoloring the ceramic can be achieved through one of two means. The first is to assure that the alloy is free from metals that migrate through the porcelain causing its discoloration. The second is to assure that any metals in the alloy that migrate through the ceramic will not discolor it because they have neutrally-colored oxides or because they react with other constituents forming bulky and non-migrating compounds. This invention also discloses a metal design that assures the absence of ceramic discoloration upon bonding to the metal at high temperature.

In metal-ceramic dental restoration, the metal serves as a strengthening substrate for the inherently weak ceramic. The metal must have sufficient mechanical strength to withstand masticatory forces without deformation to the extent of allowing fracture of the porcelain. Since the ceramic is fused to the metal at a temperature sufficient to mature the ceramic, the alloy must not deform at that temperature. Furthermore, the alloy must withstand the corrosive conditions of the mouth and it must be capable of casting by normal dental casting techniques.

For many years, special precious metal alloys, including gold alloys, satisfied the foregoing requirements very well. In recent times base metal alloys have become of considerable interest and this has been given increased impetus as a result of the greater cost of gold. A considerable number of base metal alloys have been marketed for dental purposes, many of which were developed originally for high strength, particularly strength at high temperature, and corrosion resistance. Such high strength alloys are very difficult to grind, polish and manipulate which is a significant disadvantage in dental use. In addition, the high melting temperature of such alloys make them relatively difficult to melt and cast according to dental procedures.

SUMMARY OF THE INVENTION

It is, therefore, a primary object of the present invention to provide a new and improved base metal alloy for dental use.

It is a more particular object of this invention to provide such an improved alloy for use as a substrate to which ceramic coating is applied.

It is a further object of this invention to provide such an alloy which has thermal expansion and contraction characteristics compatible with ceramic.

It is a further object of this invention to provide such an alloy which does not cause discoloration of the ceramic coating.

It is a further object of this invention to provide such an alloy which has the ability to withstand corrosive conditions of the mouth.

It is a further object of this invention to provide such an alloy which is relatively easy to grind, polish and manipulate.

It is a further object of this invention to provide such an alloy which is relatively easy to melt and cast to intricate shape using dental procedures.

It is a further object of this invention to provide such an alloy which when cast in an investment mold will have a clean appearance rendering it attractive from an aesthetic standpoint and rendering it easy to finish and polish.

The present invention provides an alloy for dental use incorporating the following ranges of constituents in percentages by weight: aluminum 0–3.0%, cobalt 0–20.0%, chromium 10.0–20.0%, manganese 0–1.5%, molybdenum 6.0–18.0%, nickel 58.5–77.0% and silicon 0-2.0% and essentially free from carbon. The alloy of the present invention possesses castability, strength properties and physical properties including melting range and coeffieicent of thermal expansion compatible with available porcelain products. The alloy of the present invention retains the corrosion resistance properties found in nickel-chromium base alloys while at the same time having reduced yield strength typical of gold alloys thereby resulting in greater ease of grinding, polishing and manipulation. The alloy of the present invention finds use as a porcelain substrate alloy and also as a crown and bridge or partial denture alloy.

DETAILED DESCRIPTION OF THE INVENTION

The relative proportions of the various elements comprising the alloy composition of the present invention enable the alloy to retain the corrosion resistance properties found in nickel-chromium base alloys while at the same time having a reduced yield strength typical of gold alloys thereby resulting in a greater ease of grinding, polishing, and manipulation. The alloy of the present invention also maintains castability, strength properties and physical properties including melting range and coefficient of thermal expansion and lack of discoloration effects compatible with available porcelain products. In particular, the alloy composition of the present invention is essentially free from carbon and contains, by weight, aluminum 0-3.0%, cobalt 0-20.0% chromium 10.0-20.0%, manganese 0-1.5%, molybdenum 6.0-18.0%, nickel 58.5-77.0% and silicon 0-2.0%. Preferred alloy compositions are those which contain by weight, aluminum 1.0-2.0%, cobalt 0-10%, chromium 12.0-16.0%, manganese 0.5-1.0%, molybdenum 8.0-16.0%, silicon 0.5-1.0% and the balance nickel.

The roles of the respective alloying elements are believed to be as follows. Chromium, present in a substantial proportion by weight, enhances the corrosion and tarnish resistance of the alloy. Nickel, the element present in a major proportion by weight, is employed not only for its resistance to corrosion but also because it serves as a good host for the chromium. A good host material for chromium is necessary to enable the alloy to be utilized in precision casting. In particular, of the three known bases for chromium in alloys of this general type, i.e. cobalt, iron or nickel bases, nickel is preferred because it provides better workability of the resulting alloy, a lower melting temperature of the alloy, and greater precision of casting as compared to the other two bases.

Control of the coefficient of thermal expansion of the alloy is essential to render the alloy compatible with porcelain. In the alloy of the present invention molybdenum is employed to control the thermal expansion and contraction characteristics thereof. For example, an alloy including nickel in an amount by weight of about 80% and chromium in an amount by weight of about 20% has a coefficient of thermal expansion of $15.5 \times 10^{-6}$/C in the temperature range of from about 20° C. to about 600° C. As illustrated in Table I, the addition of one weight percent of molybdenum to the alloy reduces the coefficient of thermal expansion by about $0.1 \times 10^{-6}$/C, and the addition of 15 weight percent molybdenum reduces the coefficient of thermal expansion by about $1.5 \times 10^{-6}$/C.

TABLE I

| Mo Addition to Illustrated 80Ni-20Cr Alloy | |
|---|---|
| Wt % Mo Added | Coefficient of Thermal Expansion |
| 0 | $15.5 \times 10^{-6}$ |
| 1 | $15.4 \times 10^{-6}$ |
| 5 | $15.1 \times 10^{-6}$ |
| 10 | $14.4 \times 10^{-6}$ |
| 15 | $13.9 \times 10^{-6}$ |
| 20 | $13.4 \times 10^{-6}$ |

Thus, an important advantage of employing molybdenum in the alloy of the present invention is the high degree of precision in control of the coefficient of thermal expansion of the alloy. Another important advantage of employing molybdenum in the alloy of the present invention in the essential absence of carbon is that even large additions thereof, i.e. in the range of 10-15 weight percent of molybdenum, do not harden the alloy substantially, i.e. the alloy remains ductile. This is illustrated further by the data of Table II wherein high ductility of the alloys in the examples is indicated by the values of the Rockwell "A" hardness obtained. Also, the alloys were observed to have the ductility required to be cold worked. The data presented in Table II was derived from an alloy containing, by weight, 20% chromium, 14% cobalt, 1.5% silicon and the balance nickel plus molybdenum.

TABLE II

| Mo Addition To Ni-20Cr-14Co-1.5Si Alloy | |
|---|---|
| Wt. % Mo Added | Rockwell "A" Hardness |
| 0 | 42 |
| 2 | 45 |
| 4 | 48 |
| 6 | 50 |
| 10 | 54 |
| 12 | 56 |

In addition to the foregoing, the presence of molybdenum in the alloy enhances the corrosion resistance characteristics of the nickel and chromium constituents. Based on visual observations, the presence of molybdenum is believed to enhance the fluidity of the melted alloy and hence its ability to be cast into intricate shapes required by dental practice. The inclusion of molybdenum also serves to lower the coefficient of thermal expansion in a manner which does not increase the melting temperature of the alloy. Alternatively, approximately one percent by weight of other elements such as niobium, tantalum and tungsten can be substituted for a part of the molybdenum if desired. In addition, in view of the substantial similarities between the effects of tungsten and molybdenum on the metallurgical transformations occuring in nickel - chromium - cobalt alloys, it is felt that most or all of the molybdenum can be replaced or substituted for by tungsten.

In the alloy of the present invention, aluminum serves as a precipitation hardener and also forms a protective oxide layer when the alloy is melted. As a result, when the alloy is cast into an investment mold, a clean light gray-colored surface finish is obtained. This is highly desirable from a commercial standpoint in that the alloy is aesthetically pleasing to dentists, technicians and the like who work with the alloy, since it facilitates further finishing and polishing. On the other hand, it has been found that when aluminum is absent from the alloy, the casting will have a rough green surface which is not aesthetically desirable.

A small amount of copper can be included in the alloy to improve fluidity. A relatively small amount of copper can be substituted for a portion of the amount of aluminum in the alloy.

Cobalt can be employed in the alloy of the present invention as a substitute for a portion of the amount of nickel therein. Cobalt serves to control the yield strength and the coefficient of thermal expansion of the alloy. Manganese is employed as a deoxidizer and to control the fluidity of the metal during casting. It also can be employed to nullify the effect of any sulfur contamination of the alloy. Silicon functions as a deoxidizer, contributes the formation of a protective coating, and controls fluidity of the metal during casting and helps insure a cleaner casting.

The alloy of the present invention is made according to standard induction melting procedures and is cast into solid cylindrical shaped, i.e. rod-like, pieces or elements which are swaged down to the proper size. The alloy alternatively could be rolled or otherwise formed into flat pieces or elements, but the solid cylindrical shape is preferred because it gives continuity to and enhances the function of the protective coating formed by certain of the alloying metals.

The alloy of the present invention is illustrated further by Examples I-XIII presented herein. Hardness data is given for each example and serves as a guide in determining useability of the alloy for dental purposes. In particular, the Rockwell A hardness values are direct readings from a Rockwell testing machine. The first value of Vickers hardness shown in each of Examples I-XIII is for a cast alloy of this invention after the porcelain application heat cycle, the data being taken with a standard diamond pyramid indenter under a one kilogram load. Since hardness is not translatable from one alloy system to another some other mechanical property must be employed to compare different systems. In the present case the 0.2% offset yield strength was used as the comparable property. The second value of Vickers hardness data in Examples I-X is for the alloy in the as cast condition, the data being taken in the same manner. This data was not available for Examples XI-XIII. The Vickers hardness data in the as cast condition provides information pertinent to the workability of the alloy, and the Vickers hardness data after the porcelain application heat cycle provides information pertinent to the ultimate use of the alloy when it resides in the patient's mouth. In each example, the hardness data used as a guide indicates that the alloy of the present invention is useable as a non-precious dental alloy.

The yield strength was measured for the alloys of all the examples by standard methods, and the 0.2% offset yield strength is given for each alloy example after the porcelain application heat cycle. It is desired that the yield strength not be too high because if it is, then it becomes difficult to grind, polish and manipulate the alloy. For example, gold-based alloys for similar dental applications have a yield strength in the neighborhood of 50,000 p.s.i. Most of the alloys disclosed herein have a yield strength below but sufficiently close to this level so as to be suitable for use in long bridge applications and other dental applications. The alloys of Examples IX, X and XII, however would be more suited for single crown applications as the yield strengths for these three are relatively low when compared to that of the gold-based alloy.

The coefficient of thermal expansion (C.T.E.) of each alloy is measured by the use of a standard dilatometer, such as an Orton dilatometer. The data is obtained as an average over the temperature range from about 600° C. down to about 20° C., i.e. on the cooling cycle which is of primary interest since behavior of the alloy as it cools down after porcelain firing is an important consideration. In each example, the coefficient of thermal expansion of the alloy according to the present invention has a value making the alloy compatible with popular, commercially available porcelains.

The alloy of the present invention was observed to have sufficient fluidity in the molten state or condition to fill an intricate mold thereby possessing the degree of castability required for dental alloys. The fact that the alloy contains nickel and chromium in substantial proportions by weight gives the alloy very little or no susceptibility to corrosion and tarnish as compared to precious alloys. The alloys of all of the examples have a melting temperature range from about 2250° F. to about 2550° F. which is sufficiently above the temperature of about 1800° F. at which porcelain is fired on the cast metal so as to avoid deformation. In addition, the melting temperature range also is sufficiently above the temperature of about 1950° F. at which pure gold in some situations is melted on the surface of the cast metal. In this regard, the alloy of the present invention even possesses an advantage over gold alloys used for the same purposes.

The alloy of the present invention is further illustrated by the following examples.

EXAMPLE I

EXAMPLE I

| Constituent | Composition In Weight % |
| --- | --- |
| Nickel | 71.0 |
| Chromium | 10.0 |
| Molybdenum | 18.0 |
| Silicon | 0.5 |
| Manganese | 0.5 |
| | |
| Rockwell "A" Hardness | 53.0 |
| Vickers Hardness (porc. cycle) | 214 |
| Vickers Hardness (as cast) | 206 |
| 0.2% Offset Yield Strength (p.c.) | 40,900 psi |
| Coeff. Thermal Expansion | $13.6 \times 10^{-6}$ |

EXAMPLE II

EXAMPLE II

| Constituent | Composition In Weight % |
| --- | --- |
| Nickel | 70.5 |
| Chromium | 12.5 |
| Molybdenum | 14.0 |
| Aluminum | 1.0 |
| Silicon | 1.5 |
| Manganese | 0.5 |
| | |
| Rockwell "A" Hardness | 51.7 |
| Vickers Hardness (porc. cycle) | 205 |
| Vickers Hardness (as cast) | 227 |
| 0.2% Offset Yield Strength (p.c.) | 43,300 psi |
| Coeff. Thermal Expansion | $13.9 \times 10^{-6}$ |

EXAMPLE III

| Constituent | Composition In Weight % |
|---|---|
| Nickel | 66.0 |
| Chromium | 13.0 |
| Molybdenum | 13.5 |
| Cobalt | 5.0 |
| Aluminum | 1.0 |
| Silicon | 1.0 |
| Manganese | 0.5 |
| Rockwell "A" Hardness | 52.7 |
| Vickers Hardness (porc. cycle) | 206 |
| Vickers Hardness (as cast) | 192 |
| 0.2% Offset Yield Strength (p.c.) | 38,900 psi |
| Coeff. Thermal Expansion | $14.4 \times 10^{-6}$ |

EXAMPLE IV

| Constituent | Composition In Weight % |
|---|---|
| Nickel | 71.0 |
| Chromium | 13.0 |
| Molybdenum | 13.5 |
| Aluminum | 1.0 |
| Silicon | 1.0 |
| Manganese | 0.5 |
| Rockwell "A" Hardness | 51.5 |
| Vickers Hardness (porc. cycle) | 196 |
| Vickers Hardness (as cast) | 213 |
| 0.2% Offset Yield Strength (p.c.) | 42,700 psi |
| Coeff. Thermal Expansion | $13.8 \times 10^{-6}$ |

EXAMPLE V

| Constituent | Composition In Weight % |
|---|---|
| Nickel | 68.5 |
| Chromium | 15.5 |
| Molybdenum | 14.0 |
| Aluminum | 1.0 |
| Silicon | 0.5 |
| Manganese | 0.5 |
| Rockwell "A" Hardness | 51.2 |
| Vickers Hardness (porc. cycle) | 195 |
| Vickers Hardness (as cast) | 180 |
| 0.2% Offset Yield Strength (p.c.) | 44,700 psi |
| Coeff. Thermal Expansion | $13.7 \times 10^{-6}$ |

EXAMPLE VI

| Constituent | Composition In Weight % |
|---|---|
| Nickel | 74.5 |
| Chromium | 12.5 |
| Molybdenum | 10.0 |
| Aluminum | 2.0 |
| Silicon | 0.5 |
| Manganese | 0.5 |
| Rockwell "A" Hardness | 51.7 |
| Vickers Hardness (porc. cycle) | 191 |
| Vickers Hardness (as cast) | 202 |
| 0.2% Offset Yield Strength (p.c.) | 35,900 psi |
| Coeff. Thermal Expansion | $14.2 \times 10^{-6}$ |

EXAMPLE VII

| Constituent | Composition In Weight % |
|---|---|
| Nickel | 75.5 |
| Chromium | 12.5 |
| Molybdenum | 8.0 |
| Aluminum | 3.0 |
| Silicon | 0.5 |
| Manganese | 0.5 |
| Rockwell "A" Hardness | 51.3 |
| Vickers Hardness (porc. cycle) | 205 |
| Vickers Hardness (as cast) | 224 |
| 0.2% Offset Yield Strength (p.c.) | 39,400 psi |
| Coeff. Thermal Expansion | $14.7 \times 10^{-6}$ |

EXAMPLE VIII

| Constituent | Composition In Weight % |
|---|---|
| Nickel | 58.5 |
| Chromium | 12.0 |
| Molybdenum | 8.0 |
| Cobalt | 20.0 |
| Aluminum | 0.5 |
| Silicon | 0.5 |
| Manganese | 0.5 |
| Rockwell "A" Hardness | 48.7 |
| Vickers Hardness (porc. cycle) | 183 |
| Vickers Hardness (as cast) | 191 |
| 0.2% Offset Yield Strength (p.c.) | 36,100 psi |
| Coeff. Thermal Expansion | $15.1 \times 10^{-6}$ |

EXAMPLE IX

| Constituent | Composition In Weight % |
|---|---|
| Nickel | 70.0 |
| Chromium | 20.0 |
| Molybdenum | 8.0 |
| Aluminum | 1.0 |
| Silicon | 0.5 |
| Manganese | 0.5 |
| Rockwell "A" Hardness | 52.0 |
| Vickers Hardness (porc. cycle) | 186 |
| Vickers Hardness (as cast) | 172 |
| 0.2% Offset Yield Strength (p.c.) | 29,800 psi |
| Coeff. Thermal Expansion | $14.8 \times 10^{-6}$ |

EXAMPLE X

| Constituent | Composition In Weight % |
|---|---|
| Nickel | 77.0 |
| Chromium | 12.5 |
| Molybdenum | 8.0 |
| Aluminum | 0.5 |
| Silicon | 2.0 |
| Rockwell "A" Hardness | 51.0 |
| Vickers Hardness (porc. cycle) | 178 |
| Vickers Hardness (as cast) | 178 |
| 0.2% Offset Yield Strength (p.c.) | 33,200 psi |
| Coeff. Thermal Expansion | $15.0 \times 10^{-6}$ |

EXAMPLE XI
EXAMPLE XI

| Constituent | Composition In Weight % |
| --- | --- |
| Nickel | 64.5 |
| Chromium | 12.0 |
| Molybdenum | 12.0 |
| Cobalt | 10.0 |
| Manganese | 1.5 |
| Vickers Hardness (porc. cycle) | 176 |
| 0.2% Offset Yield Strength (p.c.) | 33,600 psi |
| Coeff. Thermal Expansion | $14.8 \times 10^{-6}$ |

EXAMPLE XII
EXAMPLE XII

| Constituent | Composition In Weight % |
| --- | --- |
| Nickel | 63.5 |
| Chromium | 20.0 |
| Cobalt | 10.0 |
| Copper | 1.0 |
| Aluminum | 3.0 |
| Silicon | 1.5 |
| Manganese | 1.0 |
| Vickers Hardness (porc. cycle) | 191 |
| 0.2% Offset Yield Strength (p.c.) | 44,000 psi |
| Coeff. Thermal Expansion | $15.2 \times 10^{-6}$ |

EXAMPLE XIII
EXAMPLE XIII

| Constituent | Composition In Weight % |
| --- | --- |
| Nickel | 63.5 |
| Chromium | 16.0 |
| Molybdenum | 6.0 |
| Cobalt | 10.0 |
| Aluminum | 3.0 |
| Silicon | 1.5 |
| Vickers Hardness (porc. cycle) | 250 |
| 0.2% Offset Yield Strength (p.c.) | 60,000 psi |
| Coeff. Thermal Expansion | $14.8 \times 10^{-6}$ |

When used in making dental restorations and the like, the alloy of the present invention is cast to the desired shape by standard casting procedures well-known in the art. The alloy in the form supplied by the manufacturer is heated at the appropriate melting temperature until it loses its cylindrical shape and becomes somewhat oval or elliptical in cross-sectional shape, whereupon it is cast using a standard dental casting machine. The alloy of the present invention has sufficient fluidity when melted for casting to fill an intricate mold completely.

After the casting of desired shape has been formed, the cast alloy of the present invention has at least one layer of porcelain applied thereto in the making of dental restorations. This is done according to standard procedures well known in the art, and frequently the dental castings are pre-oxidized at a temperature from about 1700° F. to about 1950° F. prior to applying porcelain on the metal with the resulting oxide acting as a bonding agent between the metal and porcelain. In addition, a gold layer commonly is applied to the metal, prior to porcelainizing, by painting a gold powder slurry on the metal and then melting the gold in place at a temperature of about 1945° F. Porcelain is applied to the casting by standard firing techniques well known in the art. This is done in at least one but typically several porcelain firing cycles or bakes at a temperature range of from about 1200° F. to about 1825° F. Commercially available porcelains can be used, for example one known as Will-Ceram Porcelain marketed by Williams Gold Refining Co. Inc. of Buffalo, New York.

The alloy of the present invention retains the corrosion resistance properties found in nickel-chromium base alloys while having reduced yield strength typical of gold alloys thereby resulting in greater ease of grinding, polishing and manipulation. The alloy of the present invention possesses castability, strength properties and physical properties including melting range and coefficient of thermal expansion compatible with available porcelain products. The alloy of the present invention does not cause discoloration of the porcelain and does not sag when heated at porcelain baking temperatures. The alloy finds use as a porcelain substrate alloy and also as a crown and bridge and partial denture alloy.

It is therefore apparent that the present invention accomplishes its intended objects. While the present invention has been described in detail, this is for the purpose of illustration not limitation.

We claim:

1. An alloy for dental use consisting essentially of the following constituents in the indicated percentages by weight: aluminum 1.0-3.0%, cobalt 0-20.0%, chromium 10.0-20.0%, manganese 0.5-1.5%, molybdenum 6.0-18.0%, nickel 58.5-77.0% and silicon 0.5-2.0%, with the proviso that the total of said manganese and said silicon is at least 1.0%, but no more than 3.5%.

2. An alloy according to claim 1, consisting essentially of the following constituents in the indicated percentages by weight: aluminum 1.0-2.0%, cobalt 0-10%, chromium 12.0-16.0%, manganese 0.5-1.0%, molybdenum 8.0-16.0%, silicon 0.5-1.0% and the balance nickel.

3. An alloy according to claim 1, consisting essentially of the following constituents in the indicated percentages by weight: aluminum about 1.0%, chromium about 15.5%, manganese about 0.5%, molybdenum about 14.0%, nickel about 68.5% and silicon about 0.5%.

4. A cast alloy according to claim 1, provided with at least one layer of porcelain fired on the surface thereof.

5. An alloy for dental use consisting essentially of the following constituents in the indicated percentages by weight: aluminum about 3.0%, cobalt about 10.0%, chromium about 20.0%, copper about 1.0%, manganese about 1.0%, nickel about 63.5% and silicon about 1.5%.

6. A cast alloy according to claim 5, provided with at least one layer of porcelain fired on the surface thereof.

* * * * *